(12) United States Patent
Allen et al.

(10) Patent No.: US 10,307,397 B2
(45) Date of Patent: Jun. 4, 2019

(54) ORAL DISSOLVABLE FILM THAT INCLUDES PLANT EXTRACT

(71) Applicant: Concept Matrix Solutions, Woodland Hills, CA (US)

(72) Inventors: Eric Allen, Camarillo, CA (US); Robert Davidson, Oxnard, CA (US); Tony LaRosa, Oxnard, CA (US); David Reid, Oxnard, CA (US)

(73) Assignee: CONCEPT MATRIX SOLUTIONS, Woodland Hills, CA (US)

( * ) Notice: Subject to any disclaimer, the term of this patent is extended or adjusted under 35 U.S.C. 154(b) by 912 days.

(21) Appl. No.: 14/810,595

(22) Filed: Jul. 28, 2015

(65) Prior Publication Data
US 2016/0051510 A1 Feb. 25, 2016

Related U.S. Application Data

(60) Provisional application No. 62/029,757, filed on Jul. 28, 2014.

(51) Int. Cl.
| | |
|---|---|
| *A61K 36/185* | (2006.01) |
| *A61K 36/534* | (2006.01) |
| *A61K 31/366* | (2006.01) |
| *A61K 36/67* | (2006.01) |
| *A61K 31/05* | (2006.01) |
| *A61K 31/352* | (2006.01) |
| *A61K 9/00* | (2006.01) |
| *A61K 45/06* | (2006.01) |
| *A61K 9/70* | (2006.01) |
| *A61K 9/127* | (2006.01) |

(52) U.S. Cl.
CPC .......... *A61K 31/366* (2013.01); *A61K 9/006* (2013.01); *A61K 9/0056* (2013.01); *A61K 31/05* (2013.01); *A61K 31/352* (2013.01); *A61K 36/185* (2013.01); *A61K 36/67* (2013.01); *A61K 45/06* (2013.01); *A61K 9/127* (2013.01); *A61K 9/7007* (2013.01)

(58) Field of Classification Search
CPC ....... A61K 36/67; A61K 36/53; A61K 36/185
USPC ......................................... 424/734, 750, 776
See application file for complete search history.

(56) References Cited

U.S. PATENT DOCUMENTS

| | | | | |
|---|---|---|---|---|
| 2005/0281757 A1* | 12/2005 | Ibrahim | ............... | A61K 8/0208 424/49 |
| 2009/0004254 A1* | 1/2009 | Maibach | ............... | A61K 9/006 424/444 |
| 2009/0232872 A1* | 9/2009 | Davidson | ............. | A61K 9/0051 424/439 |
| 2011/0276522 A1* | 11/2011 | Kehoe | ................. | A61K 36/185 705/500 |

* cited by examiner

*Primary Examiner* — Christopher R Tate
*Assistant Examiner* — Deborah A Davis
(74) *Attorney, Agent, or Firm* — Carlson Caspers

(57) ABSTRACT

Films (ODFs) that include botanical extract are provided, as well as methods of making and using the same.

15 Claims, 3 Drawing Sheets

ORAL DISSOLVABLE FILM THAT INCLUDES PLANT EXTRACT

PRIORITY APPLICATION

This application claims the benefit of priority to U.S. Provisional Patent Application Ser. No. 62/029,757, filed on Jul. 28, 2014, which application is incorporated herein by reference in its entirety.

BACKGROUND

Raw Botanical Extracts (RBEs) of cannabinoids, in their concentrated form, are typically viscous oils at room temperature and pressure. These oils contain cannabinoids, plant waxes, plant lipids, and sometimes plant pigments such as chlorophylls. These RBEs present some problems for incorporation into ODFs when treated like dry, solid, crystalline active pharmaceutical ingredients (APIs). Direct incorporation in a slurry typically results in sticky mixtures that do not form viable ODFs having desirable properties like being dry to touch, easily handled and packaged, and/or easily consumed. As such, what is needed is a way to incorporate RBEs into ODFs that are dry to touch, easily handled and packaged, and/or easily consumed. What is further needed is for the ODF to be configured and formulated for the release of the active ingredient in the RBEs, in a variety of profiles (e.g., immediate release (IR), sustained release (SR), delayed release (DR), modified release (MR), extended release (XR), and controlled release (CR)).

SUMMARY

In various embodiments, the thin film described herein includes the potential to improve the onset of action, lower the dosing, and enhance the efficacy and safety profile of the active ingredient. All tablet dosage forms, softgels, and liquid formulations primarily enter the blood stream via the gastrointestinal tract, which subjects the drug to degradation from stomach acid, bile, digestive enzymes, and other effects including first-pass liver metabolism. As a result, such formulations often require higher doses and generally have a delayed onset of action. Conversely, in various embodiments, the thin film described herein can avoid these issues and yield quicker onsets of action at lower doses.

In various embodiments, the thin film described herein provides for a stable, durable and quick dissolving dosage form.

In various embodiments, the thin film described herein enables suitable dosing accuracy, since every strip is manufactured to contain a relatively precise amount of the active ingredient.

In various embodiments, the thin film described herein not only ensures more accurate administration of active ingredients but also can improve compliance due to the intuitive nature of the dosage form and its inherent ease of administration. These properties are especially beneficial for pediatric, geriatric, and neurodegenerative disease patients where proper and complete dosing can be difficult.

In various embodiments, the thin film described herein possesses the ability to dissolve rapidly without the need for water, which provides an alternative to patients with swallowing disorders and to patients suffering from nausea, such as those patients receiving chemotherapy.

In various embodiments, the thin film drug delivery has the potential to allow the development of sensitive active ingredient targets that may otherwise not be possible in tablet or liquid formulations.

Sublingual film delivers a convenient, quick-dissolving therapeutic dose contained within an abuse-deterrent film matrix that cannot be crushed or injected by patients, and rapidly absorbs under the tongue to ensure compliance.

In various embodiments, the thin film described herein can be manufactured to include a relatively high load of active ingredient. For example, the active ingredient can be present in about 25-40 wt. %. Such a relatively high load of active ingredient can be advantageous when the delivery of a high load of active ingredient is needed, especially when conventional thin films cannot be readily manufactured to include such a high load of the active ingredient.

In various embodiments, the thin film described herein incorporate RBEs into an ODF, such that the ODF is dry to touch.

In various embodiments, the thin film described herein incorporate RBEs into an ODF, such that the ODF is easily handled and packaged.

In various embodiments, the thin film described herein incorporate RBEs into an ODF, such that the ODF is easily consumed.

In various embodiments, the thin film described herein is configured and formulated for the immediate release (IR) of the active ingredient in the RBEs.

In various embodiments, the thin film described herein is configured and formulated for the sustained release (SR) of the active ingredient in the RBEs.

In various embodiments, the thin film described herein is configured and formulated for the delayed release (DR) of the active ingredient in the RBEs.

In various embodiments, the thin film described herein is configured and formulated for the modified release (MR) of the active ingredient in the RBEs.

In various embodiments, the thin film described herein is configured and formulated for the extended release (XR) of the active ingredient in the RBEs.

In various embodiments, the thin film described herein is configured and formulated for controlled release (CR) of the active ingredient in the RBEs.

In various embodiments, the thin film described herein is configured and formulated for the release of the active ingredient in the RBEs, in a variety of profiles (e.g., immediate release (IR), sustained release (SR), delayed release (DR), modified release (MR), extended release (XR), and controlled release (CR)).

The present invention provides a thin film (e.g., an oral dissolvable film) that includes: (a) solvent, (b) binder, (c) optionally a lipid, (d) emulsifier, (e) botanical extract, (f) optionally a dough conditioner, (g) optionally a flavoring agent, (h) optionally a sweetener, (i) optionally a dye or pigment, (j) a powder coating on at least one external surface, and (k) optionally a preservative. The botanical extract can optionally be at least partially encapsulated by the lipid, when present.

The present invention also provides a thin film (e.g., an oral dissolvable film) that includes: (a) about 2-24 wt. % solvent, (b) about 40-50 wt. % binder, (c) about 0-22 wt. % wt. % lipid, (d) about 3-22 wt. % emulsifier, (e) up to about 65 wt. % botanical extract, (f) about 0-15 wt. % wt. % dough conditioner, (g) about 0-10 wt. % flavoring agent, (h) about 0-40 wt. % sweetener, (i) about 0-1.0 wt. % dye or pigment, (j) about 0-20 wt. % powder coating on at least one external surface, and (k) about 0-0.1 wt. % preservative. The botanical extract can optionally be at least partially encapsulated by the lipid, when present.

The present invention also provides an orally dissolving film that includes: (a) solvent that includes water, (b) binder that includes pectin, (c) optionally a lipid that includes at least one of deodorized cocoa butter oil, fruit seed oil, and vegetable based oil, (d) emulsifier that includes at least one of glycerin, ethoxylated monoglycerides, and ethoxylated diglycerides, (e) botanical extract, (f) flavoring agent that includes mint flavoring, (g) sweetener that includes at least one of sucralose and acesulfame potassium, (h) dye or pigment that includes at least one of FD&C red, FD&C blue, and FD&C yellow, (i) a powder coating on at least one external surface, that includes at least one of talc, microcrystalline cellulose, mint flavoring, sucralose, acesulfame potassium, and tapioca starch, and (j) optionally a preservative that includes at least one of sodium benzoate, methyl paraben, propyl paraben, and sodium sorbate. The botanical extract can optionally be at least partially encapsulated by the lipid, when present.

The present invention also provides an orally dissolving film that includes: (a) about 2-24 wt. % solvent that includes water, (b) about 4-50 wt. % binder that includes pectin, (c) about 0-22 wt. % lipid that includes at least one of deodorized cocoa butter oil, fruit seed oil, and vegetable based oil, (d) about 3-22 wt. % emulsifier that includes at least one of glycerin, ethoxylated monoglycerides, and ethoxylated diglycerides, (e) up to about 65 wt. % botanical extract, (f) about 0-10 wt. % flavoring agent that includes mint flavoring, (g) about 1-40 wt. % sweetener that includes at least one of sucralose and acesulfame potassium, (h) about 0-1.0 wt. % dye or pigment that includes at least one of FD&C red, FD&C blue, and FD&C yellow, (i) about 0-20 wt. % powder coating on at least one external surface, that includes at least one of talc, microcrystalline cellulose, mint flavoring, sucralose, acesulfame potassium, and tapioca starch, and (j) about 0-0.1 wt. % preservative that includes at least one of sodium benzoate, methyl paraben, propyl paraben, and sodium sorbate. The botanical extract can optionally be at least partially encapsulated by the lipid, when present.

The present invention also provides a method of preparing a thin film (e.g., an oral dissolvable film). The method includes: (a) contacting (e.g., mixing) a lipid, emulsifier, and solvent to provide a uniform first mixture; (b) contacting an active ingredient (e.g., botanical extract) with the uniform first mixture to provide a thickened second mixture; (c) contacting a binder with the thickened second mixture to provide a slurry; and (d) hot extruding, casting, and condensing the slurry to provide the thin film; or cooling, shearing, mixing, casting, and condensing the slurry to provide the thin film.

The present invention also provides a system that includes: (a) multiple thin films (e.g., multiple oral dissolvable films), each in direct contact with at least one other thin film, and each independently described herein; (b) packaging material enclosing the multiple thin films; and (c) printed indicia located on the packaging material; wherein the multiple thin films do not readily stick to another.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
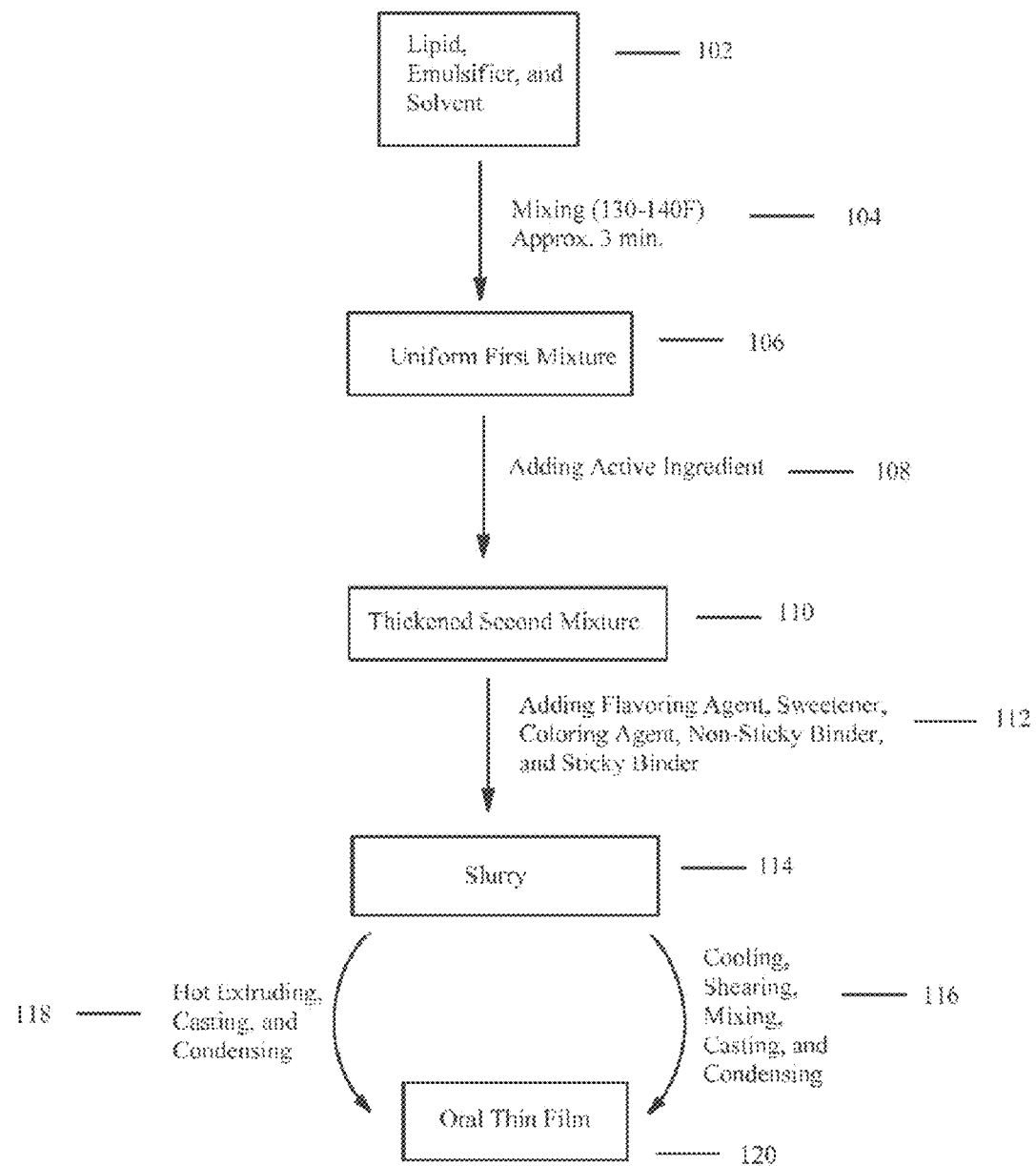
FIG. 1 illustrates a method of preparing an oral film, in various embodiments.

Reference will now be made in detail to certain claims of the invention, examples of which are illustrated in the accompanying drawings. While the invention will be described in conjunction with the enumerated claims, it will be understood that they are not intended to limit those claims. On the contrary, the invention is intended to cover all alternatives, modifications, and equivalents, which can be included within the scope of the invention as defined by the claims.

References in the specification to "one embodiment," "an embodiment," "an example embodiment," and the like, indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one of ordinary skill in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

"Oral thin film," "OTF," "oral dissolving film," "oral dissolvable film," "oral drug strip" or "oral strip" refers to a product used to administer active ingredients via absorption in the mouth (buccally or sublingually), the stomach (gastrically), and/or via the small intestines (enterically). The OTF is edible and pharmaceutically acceptable. A film is prepared typically using hydrophilic polymers that rapidly dissolves on the tongue or buccal cavity, delivering the active ingredient to the systemic circulation via dissolution when contact with liquid is made. The OTF (or more appropriately "thin film" or "TF") can also be used to adhere to mucosal tissue (e.g., at least one of mouth, nose, eye, vagina, and rectum), thereby locally delivering the active ingredient. As such, it is appreciated that those of skill in the art understand that reference to a thin film for use with mucosal tissue, such as nose, eye, vagina, and rectum, as an "oral thin film" or OTF is appropriate and acceptable.

The thin film is administered to a patient suffering from a disease or disorder in which the active ingredient (located within the thin film) is believed to treat such disease or disorder. As used herein, the term "treat" includes treating the pathology, delaying the onset of the pathology, slowing the progression of the pathology, and/or to reduce or alleviate at least one of the symptoms of the pathology.

The substances can be selected in an amount such that a desired dissolution rate can be targeted. Upon contact with mucosal tissue (including, e.g., oral mucosa) the TF will completely dissolve within the desired period of time. The period of time will vary but in reference to the oral cavity, the period of time will typically be within about 30-300 seconds.

"Multiple" refers to two or more (e.g., 2, 3, 4, 5, 6, etc.).

"Solvent" refers to a substance capable of dissolving another substance (a solute), resulting in a solution. When one substance is dissolved into another, a solution is formed. This is opposed to the situation when the compounds are insoluble like sand in water. In solution, all of the ingredients are uniformly distributed at a molecular level and no residue remains. The mixing is referred to as miscibility, whereas the ability to dissolve one compound into another is known as solubility. However, in addition to mixing, both substances in the solution interact with each other. When something is dissolved, molecules of the solvent arrange themselves around molecules of the solute. Heat is involved and entropy is increased making the solution more thermodynamically stable than the solute alone. This arrangement is mediated by the respective chemical properties of the solvent and solute, such as hydrogen bonding, dipole moment and polarizability.

In particular reference to the thin films described herein, the solvent will typically dissolve, but may also suspend, the active ingredient and other substances present in the OTF. During the condensing step, much (if not all) of the solvent can be removed. However, any solvent remaining will become an integral part of the OTF.

"Binder" refers to any material or substance that holds or draws other materials together to form a cohesive whole. Liquid binders are added to a dry substance in order to draw it together in such a way that it maintains a uniform consistency. The binder can also add mucoadhesion to the OTF.

The thin film described herein can optionally further include a mucoadhesive agent. The mucoadhesive agent, when placed in the oral cavity in contact with the mucosa therein, adheres to the mucosa. The mucoadhesive agent is especially effective in transmucosal delivery of the active ingredient, as the mucoadhesive agent permits a close and extended contact of the composition with the mucosal surface by promoting adherence of the composition or drug to the mucosa, and facilitates the release of the active ingredient from the composition. The mucoadhesive agent can be a polymeric compound, such as a cellulose derivative but it may be also a natural gum, alginate, pectin, or such similar polymer. The concentration of the mucoadhesive agent in the coating, such as a powder matrix coating, may be adjusted to vary the length of time that the film adheres to the mucosa or to vary the adhesive forces generated between the film and mucosa. The mucoadhesive agent may adhere to oral mucosa or to mucosa or tissue in other parts of the body, including the mouth, nose, eyes, vagina, and rectum. Mucoadhesive agents include, e.g., carboxymethylcellulose, polyvinyl alcohol, polyvinyl pyrrolidone (povidone), sodium alginate, methyl cellulose, hydroxyl propyl cellulose, hydroxypropylmethyl cellulose, polyethylene glycols, carbopol, polycarbophil, carboxyvinyl copolymers, propylene glycol alginate, alginic acid, methyl methacrylate copolymers, tragacanth gum, guar gum, karaya gum, ethylene vinyl acetate, dimenthylpolysiloxanes, polyoxyalkylene block copolymers, pectin, chitosan, carrageenan, xanthan gum, gellan gum, locust bean gum, and hydroxyethylmethacrylate copolymers.

"Lipid" refers to a group of naturally occurring molecules that include fats, waxes, sterols, fat-soluble vitamins (such as vitamins A, D, E, and K), monoglycerides, diglycerides, triglycerides, phospholipids, and others. The compounds are hydrophobic or amphiphilic small molecules. The amphiphilic nature of some lipids allows them to form structures such as vesicles, liposomes, or membranes in an aqueous environment. Biological lipids originate entirely or in part from two distinct types of biochemical subunits or "building-blocks": ketoacyl and isoprene groups. Using this approach, lipids may be divided into eight categories: fatty acids, glycerolipids, glycerophospholipids, sphingolipids, saccharolipids, and polyketides (derived from condensation of ketoacyl subunits); and sterol lipids and prenol lipids (derived from condensation of isoprene subunits).

Although the term lipid is sometimes used as a synonym for fats, fats are a subgroup of lipids called triglycerides. Lipids also encompass molecules such as fatty acids and their derivatives (including tri-, di-, monoglycerides, and phospholipids), as well as other sterol-containing metabolites such as cholesterol.

In particular reference to the thin films described herein, the lipids facilitate for the formation of liposomes and micelles.

Liposomes are spherical, lipid bilayer vesicles made from amphiphilic lipids. Typically these are phospholipids that are comprised of a glycerin core with two fatty acid esters, and a phosphate group bound to an additional polar group. These phospholipids thus have two lipophilic tails and a single hydrophilic head. Single fatty acid chains with a single hydrophilic head, like typical soap and detergent molecules, will preferentially form unilayer micelles and not bilayer liposomal structures.

Liposomes can be unilamellar, with a single lipid bilayer making a single sphere. They can also form various multilamellar structures. Multilamellar structures can be concentric spheres, or a sphere containing multiple unilamellar spheres within. All combinations of the above have been documented.

Figure 2:
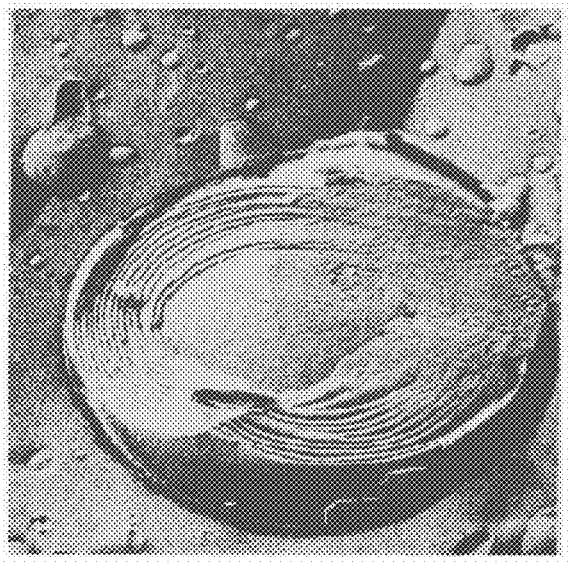
FIG. 2 illustrates a SEM micrograph of a multilamellar liposome structure made up of a set of concentric liposomal spheres.

FIG. 2 is a SEM micrograph of a multilamellar liposome structure made up of a set of concentric liposomal spheres.

Figure 3:
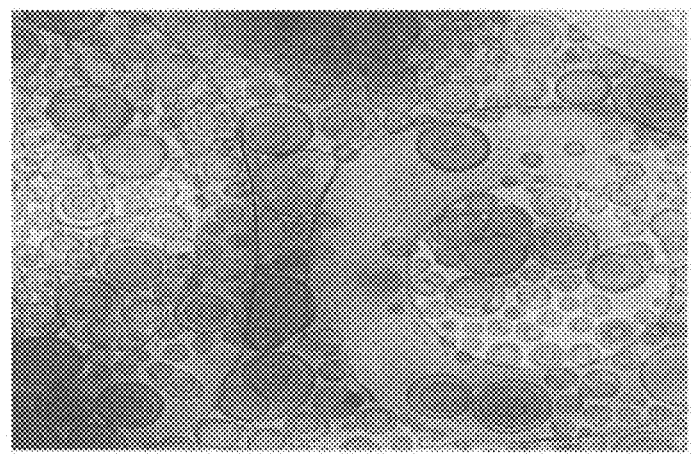
FIG. 3 illustrates a variety of unilamellar and multilamellar liposomal structures.

FIG. 3 illustrates a variety of unilamellar and multilamellar liposomal structures.

Figure 4:
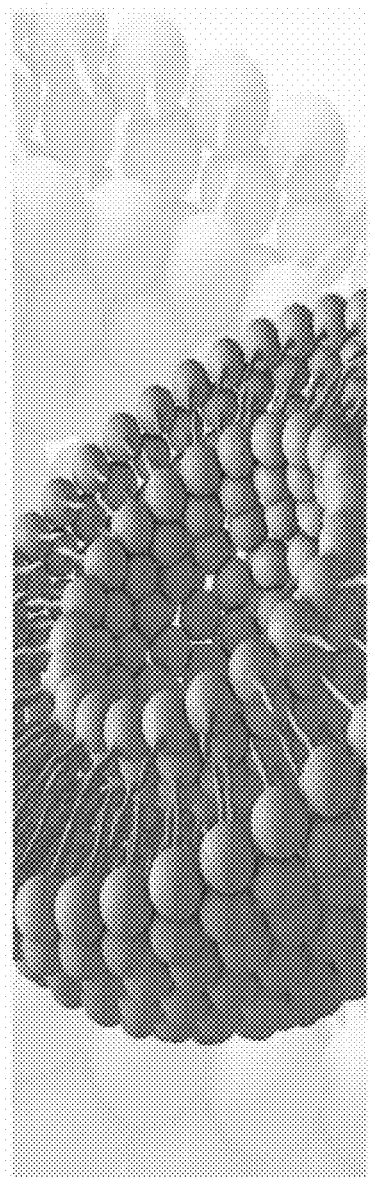
FIG. 4 illustrates a diagrammatic representation of a unilamellar liposome.

FIG. 4 is a diagrammatic representation of a unilamellar liposome. Note that as the distance from the center of the liposome increases, the density of the atoms decreases. This leads to tight grouping of the polar heads on the interior surface of the lipid bilayer and a looser grouping of polar heads and tails on the outer surface. The addition of non-polar lipids, like triacyl glycerides (standard fats), cholesterol, or tocopherol, can stabilize the bilayer structure by filling in gaps that the amphiphilic lipids by themselves cannot easily fill.

The interior aqueous capsule in the center of a unilamellar liposome can contain water—as well as water soluble atoms or molecules. Likewise, the aqueous layers between the lipid bilayers of a multilamellar liposome structure can contain the same water soluble atoms or molecules as the center capsule. The interstitial aqueous environment exterior to the liposomes can contain the same or different aqueous solutions.

The interior of the lipid bilayer is an environment that acts as an organic solvent, and it will hold lipophilic molecules in solution within the layer. Thus, liposomes contain both lipophilic and hydrophilic solvation environments and can act as carriers of various aqueous and organic molecules.

Liposomes in close proximity to one another can merge to form larger liposome structures. When the interstitial aqueous phase is partially or completely evaporated, liposomes will necessarily come into very close contact with each other. Adding heat can make a liposome's membrane less rigid and more apt to merge with neighboring liposomes.

Liposomes will form when amphiphilic phospholipids are high-shear stirred in an aqueous environment. If fats or other organic materials are included in the process, then they be-come part of the lipid bilayers that make up the liposome's bilayer membrane. Material dissolved in the aqueous phase will become incorporated into the aqueous phases of the liposomal structures as well. High shear mixing yields predominantly unilamellar liposomes. Low shear yields various combinations of unilamellar and multilamellar liposomal structures.

"Encapsulated" refers to the enclosure of a first compound (e.g., active ingredient) by a second compound (e.g., lipid). As described herein, the second compound (e.g., lipid) can encapsulate the first compound (e.g., active ingredient) by the formation of liposomes and/or micelles.

"Emulsifier" refers to a substance capable of forming or promoting an emulsion. An emulsion is a mixture of two or more liquids that are normally immiscible (nonmixable or unblendable). Emulsions are part of a more general class of two-phase systems of matter called colloids. Although the terms colloid and emulsion are sometimes used interchangeably, emulsion should be used when both the dispersed and the continuous phase are liquids. In an emulsion, one liquid (the dispersed phase) is dispersed in the other (the continuous phase). Examples of emulsions include vinaigrettes, milk, mayonnaise, and some cutting fluids for metal working. The photo-sensitive side of photographic film is an example of a colloid.

In particular reference to the thin films described herein, the emulsifier promotes the separation of phases (e.g., aqueous and lipids), while allowing them to be mixed.

"Active ingredient" refers to botanical extracts of plant matter (alternatively referred to as "raw botanical extracts (RBEs)" or "raw botanical extracts (RBEs) of cannabinoids"). The thin film can be administered, e.g., to a human patient in need of a treatment of a disease or disorder by the administration of the active ingredient (botanical extract). The botanical extract can include kavalactones, tetrahydrocannabinols (THCs) (the isomers of tetrahydrocannabinol), cannabidiol (CBD), and/or cannabinoids. For example, the kava plant will typically include the active ingredients kavalactones. Likewise, the cannabis plant will typically include the active ingredients tetrahydrocannabinols (THCs) and cannabidiol (CBD).

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The term "botanical extract" or "raw botanical extract (RBE)" refers to a concentrate of plant tissue (e.g., cannabis or kava), typically a viscous oil at ambient temperature and standard pressure. The plant can be cannabis, such that the RBE can be a "botanical extract of cannabinoids" or "cannabinoid botanical extract." The concentrate can be obtained, e.g., by the extraction (e.g., hot solvent extraction, supercritical fluid extraction, etc.) of the plant tissue (e.g., cannabis leaf or kava root root). The botanical extract will include the desired components of the cannabis plant, e.g., kavalactones, tetrahydrocannabinols (THCs), cannabidiol (CBD), and/or cannabinoids. The extract can subsequently be purified employing, e.g., at least one of filtration (e.g., charcoal filter), chromatography (e.g., HPLC), distillation, etc. The purification can be carried out to remove at least a portion of the undesirable components of the plant, e.g., plant waxes, plant lipids, and/or plant pigments such as chlorophylls, present in the extract.

The active ingredient can be present in any suitable and appropriate amount, depending upon the desired dosing. For example, in a 100 mg thin film, the active ingredient can be present in an amount of about 0.01-60 mg, about 0.1-50 mg, or about 0.5-40 mg.

"Flavoring agent" refers to a substance capable of providing a flavor. In addition to providing a palatable and pleasurable factor to the user, the flavoring agent can also mask undesirable flavors present in the OTF. In specific embodiments, the flavoring agent includes mint flavoring.

"Flavor extract" refers to a flavoring agent obtained by extracting a part of a raw material, often by using a solvent such as ethanol or water. The majority of natural essences are obtained by extracting the essential oil from the blossoms, fruit, roots, etc., or the whole plants, through four techniques: expression (when the oil is very plentiful and easily obtained, as in lemon peel), absorption (generally accomplished by steeping in alcohol, as vanilla beans), maceration (used to create smaller bits of the whole, as in making peppermint extract, etc.), and distillation (used with maceration, but in many cases, it requires expert chemical knowledge and the erection of costly stills).

"Sweetener" refers to a substance capable of providing a palatable and pleasurable factor to the user, and/or capable of masking undesirable flavors present in the OTF. In specific embodiments, the sweetener includes at least one of sucralose and acesulfame potassium.

"Bitter blocker" refers to a substance capable of blocking or diminishing the bitter taste of another substance.

"Palatable" refers to a substance (e.g., oral thin film) being relatively acceptable or agreeable to the palate or taste (e.g., sweet or savory), and in some cases to the olfactory nerves.

"Dye or pigment" refers to a substance that imparts coloring and/or aesthetic appearance to the OTF. A dye is a colored substance that has an affinity to the substrate to which it is being applied. The dye is generally applied in an aqueous solution, and requires a mordant to improve the fastness of the dye on the fiber. A pigment is a material that changes the color of reflected or transmitted light as the result of wavelength-selective absorption. This physical process differs from fluorescence, phosphorescence, and other forms of luminescence, in which a material emits light. Both dyes and pigments appear to be colored because they absorb some wavelengths of light more than others. In contrast with a dye, a pigment generally is insoluble, and has no affinity for the substrate. Some dyes can be precipitated with an inert salt to produce a lake pigment, and based on the salt used they could be aluminum lake, calcium lake or barium lake pigments. In specific embodiments, the dye or pigment includes at least one of FD&C red, FD&C blue, and FD&C yellow.

"Preservative" refers to an agent that extends the storage life of food and non-food products by retarding or preventing deterioration of flavor, odor, color, texture, appearance, nutritive value, or safety. A preservative need not provide a lethal, irreversible action resulting in partial or complete microbial cell destruction or incapacitation. Sterilants, sanitizers, disinfectants, sporicides, viracides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than killing microorganisms) and exposure time (a preservative has days to months to act whereas a sanitizer has at most a few minutes to act). In specific embodiments, the preservative includes at least one of sodium benzoate, methyl paraben, propyl paraben, and sodium sorbate.

"Powder coating" refers to a substance that when used on the external surface of an OTF, prevents, minimizes and/or mitigates the likelihood that the OTF will stick to another adjoining OTF once packaged and/or manufacturing equipment. As such, the powder coating can serve as a processing aid. The powder coating can also provide a vehicle for additional flavoring. The size of the substances present in the powder coating can vary as desired, but will typically be in the range of about 1 μm to about 100 μm. In specific embodiments, the powder coating is present on at least one external surface, and includes at least one of talc, microcrystalline cellulose, mint flavoring, sucralose, acesulfame potassium, and tapioca starch.

"Tensile strength" refers to the maximum stress that a material can withstand while being stretched or pulled before failing or breaking. Tensile strength is the opposite of compressive strength and the values can be quite different. Tensile strength is defined as a stress, which is measured as force per unit area. For some non-homogeneous materials (or for assembled components) it can be reported just as a force or as a force per unit width. In the SI system, the unit is the pascal (Pa) (or a multiple thereof, often megapascals (MPa), using the mega- prefix); or, equivalently to pascals, newtons per square meter ($N/m^2$). The customary unit is pounds-force per square inch ($lbf/in^2$ or psi), or kilo-pounds per square inch (ksi, or sometimes kpsi), which is equal to 1000 psi; kilo-pounds per square inch are commonly used for convenience when measuring tensile strengths. Typically, the testing involves taking a small sample with a fixed cross-section area, and then pulling it with a controlled, gradually increasing force until the sample changes shape or breaks.

"Pliable" refers to the ability of an article to readily bend, be flexible, or to be supple.

"Non-sticky" refers to an article (e.g., thin film) not having the property of readily adhering or sticking to another surface (e.g., another article, manufacturing equipment, packaging material, the user, etc.).

"Soft" refers to an article being relatively smooth and agreeable to the touch; not rough or coarse. Such an article will be capable of producing agreeable sensations, pleasant or comfortable, upon contact with an animal such as a human.

"Chewable configuration" refers to an article being manufactured in such a manner and with ingredients, that it possesses a configuration capable of being readily chewed by an animal, such as a human.

"Malleable configuration" refers to refers to an article being manufactured in such a manner and with ingredients, that it possesses a configuration capable of being readily shaped or changed in form (e.g., folded, bent, rolled, twisted, flexed, etc.) without breaking.

"Ductile property" refers to the ability of an article (e.g., thin film) being readily shaped or changed in form (e.g., folded, bent, rolled, twisted, flexed, etc.) without breaking.

"Mixing" refers to the act of combining, uniting, and/or joining multiple substances, into one mass, collection, or assemblage (e.g., slurry), generally with a thorough and continuous contacting of the constituents.

"Blending" refers to the act of mixing that employs equipment typically referred to as a blender, or any device capable of blending a mixture. The mixing can provide a relatively smooth mixture, where the constituents are inseparable. When used in the context of "high shear blending", the blender has sharp edged blades and is used at high speed (1000-10,000 rpm).

"Mixture" refers to the mass, collection, or assemblage (e.g., slurry) obtained from the act of mixing.

"Cooling" refers to the act of removing or transferring a sufficient amount of energy (e.g., thermal energy), within a suitable period of time, such that a decrease in temperature is experienced.

"Shearing" refers to the act of blending using sharp edged blending/mixing blades.

"Slurry" refers to a relatively viscous mixture, but it flows freely. Upon condensing, the slurry will form a film.

As used herein, "contacting" refers to the act of touching, making contact, or of bringing substances into immediate proximity.

"Hot extruding" refers to the act of extruding an article, while the article is currently being heated, or was previously heated, such that the article is at an elevated temperature during the extruding process. The extruding process typically includes forcing the article through a die, thereby obtaining a desired cross-section.

"Casting" or "film casting" refers to the act of removing liquid (e.g., water and/or solvent) from a mixture (e.g., slurry), such that a film is produced.

"Condensing" refers to the act of removing liquid (e.g., water and/or solvent).

"Heating" refers to the act of applying or transferring a sufficient amount of energy (e.g., thermal energy), within a suitable period of time, such that a rise in temperature is experienced.

"Conductive heat transfer" or "conduction" refers to the transfer of heat from one condensed material into another condensed material that does not involve bulk motion within either of the condensed media.

"Radiative heat transfer" or "radiation" refers to the transfer of heat from one article to another by way of electromagnetic means, usually by infrared radiation, but can also be microwave radiation.

"Convective heat transfer" or "convection" refers to the transfer of heat from one article to another, by the movement of fluids. Convection is usually the dominant form of heat transfer in liquids and gases. Although often discussed as a distinct method of heat transfer, convective heat transfer involves the combined processes of conduction (heat diffusion) and advection (heat transfer by bulk fluid flow).

Convection can be "forced" by movement of a fluid by means other than buoyancy forces (for example, a water pump in an automobile engine). In some cases, natural buoyancy forces alone are entirely responsible for fluid motion when the fluid is heated, and this process is called "natural convection." An example is the draft in a chimney or around any fire. In natural convection, an increase in temperature produces a reduction in density, which causes fluid motion due to pressures and forces when fluids of different densities are affected by gravity (or any g-force). For example, when water is heated on a stove, hot water from the bottom of the pan rises, displacing the colder denser liquid which falls. After heating has stopped, mixing and conduction from this natural convection eventually result in a nearly homogeneous density, and even temperature.

Two types of convective heat transfer can be distinguished: free or natural convection (passive) and forced convection (active). Active convection occurs when a fluid is forced to flow over the surface by an external source such as fans, by stirring, and pumps, creating an artificially induced convection current. Passive convention occurs when fluid motion is caused by buoyancy forces that result from the density variations due to variations of temperature in the fluid. In the absence of an external source, when the fluid is in contact with a hot surface, its molecules separate and scatter, causing the fluid to be less dense. As a consequence, the fluid is displaced while the cooler fluid gets denser and the fluid sinks. Thus, the hotter volume transfers heat towards the cooler volume of that fluid. Familiar examples are the upward flow of air due to a fire or hot object and the circulation of water in a pot that is heated from below.

"In vacuo" refers to under vacuum. The vacuum can be a partial vacuum or a complete vacuum. Typically, the vacuum will be a partial vacuum (e.g., a reduced pressure) such as, e.g., a pressure of less than about 30 mm mercury (Hg). Specifically, the reduced pressure can be less than about 29 mm mercury (Hg). More specifically, the reduced pressure can be about 10 to about 29 mm of mercury (Hg).

"Packaging material" refers to those materials and substances employed to package the product (e.g., thin film). Such materials are widely known to those of skill in the art.

"Enclosing" refers to the packaging materials containing or holding the product (e.g., thin film) by surrounding the product with the packaging material. The packaging materials can partially surround the product, or can completely surround the product. Typically, to ensure safety (e.g., no tampering with product) and freshness, the packaging materials will completely surround the product. For example, the packaging materials can form a relatively vapor impermeable enclosure of the product.

"Printed indicia" refers to a marking, image, text, and/or symbol located on the surface of the packaging material. The indicia can be placed on the surface of the packaging material by any suitable means (e.g., ink printing, laser printing, etc.). The indicia can include, e.g., a printed message or instructions, list of ingredients (active and inactive), weight of product, manufacturer name and address, manufacturer trademark, etc.

Referring to FIG. 1, an example of a block flow diagram illustrating a method of preparing an oral thin film (100) is shown, according to some embodiments. A combination of lipid, emulsifier, and solvent (102) is mixed to provide a uniform first mixture (106). Active ingredient is added (108) to the uniform first mixture (106), to form a thickened second mixture (110). Flavoring agent, sweetener, coloring agent, non-sticky binder, and sticky binder are added to the thickened second mixture (110), to provide a slurry (114). The slurry (114) is cooled, sheared, mixed, cast, and condensed (116) to provide an oral thin film (120). Alternatively, the slurry (114) is hot extruded, cast, and condensed (118) to provide an oral thin film (120).

The combination of lipid, emulsifier, and solvent (102) is mixed (104) to provide a uniform first mixture (106). The mixing (104) will typically be carried out at an elevated temperature (e.g., about 130-140° F. or 54.4-60° C.), sufficient to provide the uniform first mixture (106). Additionally, mixing (104) will typically be carried out for a suitable period of time (e.g., about 3 minutes), sufficient to provide the uniform first mixture (106). The mixing (104) can be carried out in any suitable manner, employing suitable equipment known to those of skill in the art, sufficient to provide the uniform first mixture (106). For example, the mixing (104) can include blending, which can be carried out employing a blender.

The uniform first mixture (106) and active ingredient can be contacted (108), to provide a thickened second mixture (110). Typically, the active ingredient can be added (108) to the uniform first mixture (106). The contacting (108) can include mixing. The mixing (108) will typically be carried out at room temperature (e.g., about 70° F.), and for a suitable period of time (e.g., up to about 5 minutes), sufficient to provide the thickened second mixture (110). The mixing (108) can be carried out in any suitable manner, employing suitable equipment known to those of skill in the art, sufficient to provide the thickened second mixture (110). For example, the mixing (108) can include blending, which can be carried out employing a blender.

Flavoring agent, sweetener, coloring agent, non-sticky binder, and sticky binder are contacted with the thickened second mixture (110), to provide a slurry (114). Typically, the flavoring agent, sweetener, coloring agent, non-sticky binder, and sticky binder can be added (112) to the thickened second mixture (110), to provide a slurry (114). The contacting can include mixing. The mixing will typically be carried out at room temperature (e.g., about 70° F.), and for a suitable period of time (e.g., up to about 5 minutes), sufficient to provide the slurry (114). The mixing can be carried out in any suitable manner, employing suitable equipment known to those of skill in the art, sufficient to provide the slurry (114). For example, the mixing can include blending, which can be carried out employing a blender.

The slurry (114) is hot extruded, cast, and condensed (118), to provide the thin film (120). With some active ingredients (e.g., caffeine), upon cooling, the active ingredient will fall out of solution (i.e., precipitate), due to poor solubility issues. With such active ingredients, the slurry (114) can be cooled, sheared, mixed, cast, and condensed (116) to provide the thin film (120).

The slurry (114) will typically have up to about 85 wt. % water. As such, the condensing can be carried out until the thin film (120) has the requisite amount of water (e.g., about 4-18 wt. %). Typically, the condensing will be carried out at an elevated temperature (e.g., at least about 70° C. (158° F.)). Additionally, the condensing will typically be carried out for an extended period of time (e.g., at least about 10 minutes). The condensing can be carried out in any suitable manner, employing suitable equipment known to those of skill in the art, sufficient to provide the thin film (120). For example, the condensing can be carried out employing an oven that utilizes passive convection. Alternatively, the condensing can be carried out employing an oven that utilizes active convection. In addition to (or in replace of) the elevated temperature, the condensing can be carried out at a reduced pressure (e.g., in vacuo).

Specific ranges, values, and embodiments provided below are for illustration purposes only and do not otherwise limit the scope of the invention, as defined by the claims. The specific ranges, values, and embodiments described below encompass all combinations and sub-combinations of each disclosed range, value, and embodiment, whether or not expressly described as such.

Specific Ranges, Values, and Embodiments

In specific embodiments, the thin film is an oral thin film (OTF).

In specific embodiments, the thin film is an oral dissolvable film (ODF).

In specific embodiments, the thin film is an oral thin film, which is edible and pharmaceutically safe and effective.

In specific embodiments, the thin film is configured for application to mucosal tissue or a mucosal surface.

In specific embodiments, the thin film is configured for application to at least one of the mouth, buccal cavity, nose, eye, vagina, and rectum.

In specific embodiments, the thin film is configured for application to the mouth.

In specific embodiments, the thin film is configured for application to the buccal cavity.

In specific embodiments, the thin film is configured for application to the nose.

In specific embodiments, the thin film is configured for application to the eye.

In specific embodiments, the thin film is configured for application to the vagina.

In specific embodiments, the thin film is configured for application to the rectum.

In specific embodiments, the thin film is configured for delivering the active ingredient to at least one of the mouth, buccal cavity, nose, eye, vagina, and rectum.

In specific embodiments, the thin film is configured for delivering the active ingredient to the mouth.

In specific embodiments, the thin film is configured for delivering the active ingredient to the buccal cavity.

In specific embodiments, the thin film is configured for delivering the active ingredient to the nose.

In specific embodiments, the thin film is configured for delivering the active ingredient to the eye.

In specific embodiments, the thin film is configured for delivering the active ingredient to the vagina.

In specific embodiments, the thin film is configured for delivering the active ingredient to the rectum.

In specific embodiments, the solvent includes at least one of water and ethanol.

In specific embodiments, the solvent includes water and ethanol.

In specific embodiments, the solvent includes water.

In specific embodiments, the solvent includes ethanol.

In specific embodiments, the solvent is present in at least about 2 wt. %.

In specific embodiments, the solvent is present in up to about 24 wt. %.

In specific embodiments, the solvent is present in about 2-24 wt. %.

In specific embodiments, the solvent is present in at least about 4 wt. %.

In specific embodiments, the solvent is present in up to 12 wt. %.

In specific embodiments, the solvent is present in about 4-12 wt. %.

In specific embodiments, the solvent is present in about 8 wt. %.

In specific embodiments, the binder includes at least one of pectin, microcrystalline cellulose, xanthan gum, locust bean gum, guar gum, gum arabic, gum tragacanth, gum karaya, beta glucan, glucomannan, tapioca starch, carrageenan, xanthan gum, gellan gum, alginic acid or sodium alginate, konjac gum, tara gum, chitosan, agar, maltodextrin, polyvinyl alcohol, pullulan, polycarbophil, povidone, hydroxypropyl methylcellulose, hydroxypropyl cellulose, hydroxypropyl starch, and polyethylene glycol.

In specific embodiments, the binder is acidic.

In specific embodiments, the binder includes at least one of pectin and microcrystalline cellulose.

In specific embodiments, the binder includes pectin.

In specific embodiments, the binder includes microcrystalline cellulose.

In specific embodiments, the binder is sticky.

In specific embodiments, the binder is non-sticky.

In specific embodiments, the binder is present in at least about 4 wt. %.

In specific embodiments, the binder is present in up to about 50 wt. %.

In specific embodiments, the binder is present in about 4-50 wt. %.

In specific embodiments, the binder is present in at least about 10 wt. %.

In specific embodiments, the binder is present in up to about 36 wt. %

In specific embodiments, the binder is present in about 10-36 wt. %.

In specific embodiments, the binder is present in about 25 wt. %.

In specific embodiments, the lipid is absent.

In specific embodiments, the lipid is present.

In specific embodiments, the lipid includes at least one of almond oil, argan oil, avocado oil, canola oil, cashew oil, castor oil, cocoa butter (e.g., deodorized cocoa butter oil), coconut oil, colza oil, corn oil, cottonseed oil, grape seed oil, hazelnut oil, hemp oil, hydroxylated lecithin, lecithin, linseed oil, macadamia oil, mango butter, marula oil, mongongo nut oil, olive oil, palm kernel oil, palm oil, peanut oil, pecan oil, perilla oil, pine nut oil, pistachio oil, poppy seed oil, pumpkin seed oil, rice bran oil, safflower oil, sesame oil, shea butter, soybean oil, sunflower oil, walnut oil, grape seed oil, and watermelon seed oil.

In specific embodiments, the lipid includes at least one of hydroxylated lecithin and deodorized cocoa butter oil.

In specific embodiments, the lipid includes hydroxylated lecithin.

In specific embodiments, the lipid includes deodorized cocoa butter oil.

In specific embodiments, the lipid is present in at least about 4 wt. %.

In specific embodiments, the lipid is present in up to about 22 wt. %.

In specific embodiments, the lipid is present in about 0-22 wt. %.

In specific embodiments, the lipid is present in about 4-22 wt. %.

In specific embodiments, the lipid is present in at least about 10 wt. %.

In specific embodiments, the lipid is present in up to about 18 wt. %.

In specific embodiments, the lipid is present in about 10-18 wt. %.

In specific embodiments, the lipid is present in about 14.8 wt. %.

In specific embodiments, the emulsifier includes at least one of glycerin, ethoxylated monoglycerides, and ethoxylated diglycerides.

In specific embodiments, the emulsifier includes at least one of glycerin, propylene glycol, and polyethylene glycol.

In specific embodiments, the emulsifier includes glycerin.

In specific embodiments, the emulsifier is present in at least about 3 wt. %.

In specific embodiments, the emulsifier is present in up to about 22 wt. %.

In specific embodiments, the emulsifier is present in about 3-22 wt. %.

In specific embodiments, the emulsifier is present in at least about 8 wt. %.

In specific embodiments, the emulsifier is present in up to about 18 wt. %.

In specific embodiments, the emulsifier is present in about 8-18 wt. %.

In specific embodiments, the emulsifier is present in about 14 wt. %.

In specific embodiments, the thin film further includes an absorption enhancer.

In specific embodiments, the thin film further includes a flavoring agent.

In specific embodiments, the flavoring agent includes at least one of a liquid flavor extract and a solid flavor extract.

In specific embodiments, the flavoring agent includes a liquid flavor extract.

In specific embodiments, the flavoring agent includes a solid flavor extract.

In specific embodiments, the thin film further includes a sweetener.

In specific embodiments, the sweetener includes at least one of sucralose, acesulfame potassium, ammonium glycyrrhizinate, naringin dihydrochalcone, neohesperidin dihydrochalcone, neotame, erythritol, xylitol, sucrose, sodium saccharine, stevia, alitame, fructose, sucralose, and aspartame.

In specific embodiments, the sweetener includes at least one of sucralose, acesulfame potassium, and ammonium glycyrrhizinate.

In specific embodiments, the sweetener includes at least one of sucralose and acesulfame potassium.

In specific embodiments, the sweetener is present in at least about 1 wt. %.

In specific embodiments, the sweetener is present in up to about 40 wt. %.

In specific embodiments, the sweetener is present in about 1-40 wt. %.

In specific embodiments, the sweetener is present in at least about 6 wt. %.

In specific embodiments, the sweetener is present in up to about 14 wt. %.

In specific embodiments, the sweetener is present in about 6-14 wt. %.

In specific embodiments, the sweetener is present in about 10 wt. %.

In specific embodiments, the thin film further includes a dye or pigment.

In specific embodiments, the dye or pigment includes at least one of FD&C food colorings and vegetable derived food colorings.

In specific embodiments, the dye or pigment includes FD&C food colorings (e.g., FD&C red, FD&C blue, and/or FD&C yellow).

In specific embodiments, the dye or pigment includes vegetable derived food colorings.

In specific embodiments, the dye or pigment is present in up to about 0.1 wt. %.

In specific embodiments, the dye or pigment is present in about 0-0.1 wt. %.

In specific embodiments, the dye or pigment is present in at least about 0.01 wt. %.

In specific embodiments, the dye or pigment is present in up to about 0.04 wt. %.

In specific embodiments, the dye or pigment is present in about 0.01-0.04 wt. %.

In specific embodiments, the dye or pigment is present in about 0.2 wt. %.

In specific embodiments, the thin film further includes a preservative.

In specific embodiments, the preservative includes at least one of benzoate salt, sorbate salt, and natamycin.

In specific embodiments, the preservative includes sodium benzoate.

In specific embodiments, the preservative includes at least one of sodium benzoate, methyl paraben, propyl paraben, and sodium sorbate.

In specific embodiments, the preservative is present in up to about 0.1 wt. %.

In specific embodiments, the preservative is present in about 0-0.1 wt. %.

In specific embodiments, the preservative is present in up to about 0.02 wt. %.

In specific embodiments, the preservative is present in about 0-0.02 wt. %.

In specific embodiments, the dough conditioner includes at least one of glycerin, ethoxylated monoglycerides, and ethoxylated diglycerides.

In specific embodiments, the dough conditioner includes glycerin.

In specific embodiments, the dough conditioner includes ethoxylated monoglycerides.

In specific embodiments, the dough conditioner includes ethoxylated diglycerides.

In specific embodiments, the dough conditioner is present in about 0-25 wt. %.

In specific embodiments, the dough conditioner is present in about 1-25 wt. %.

In specific embodiments, the dough conditioner is present in about 1-15 wt. %.

In specific embodiments, the thin film further includes a powder coating.

In specific embodiments, the powder coating includes at least one of talc, microcrystalline cellulose, powdered flavoring agent, powdered sweetener, and powdered tapioca starch.

In specific embodiments, the powder coating includes at least one of talc and microcrystalline cellulose.

In specific embodiments, the powder coating includes talc and microcrystalline cellulose.

In specific embodiments, the powder coating is present in up to about 20 wt. %.

In specific embodiments, the powder coating is present in about 0-20 wt. %.

In specific embodiments, the powder coating is present in at least about 5 wt. %.

In specific embodiments, the powder coating is present in up to about 15 wt. %.

In specific embodiments, the powder coating is present in about 5-15 wt. %.

In specific embodiments, the powder coating is present in about 10 wt. %.

In specific embodiments, the botanical extract includes less than about 5 wt. % plant waxes.

In specific embodiments, the botanical extract includes less than about 1 wt. % plant waxes.

In specific embodiments, the botanical extract includes less than about 0.5 wt. % plant waxes.

In specific embodiments, the botanical extract includes less than about 5 wt. % plant lipids.

In specific embodiments, the botanical extract includes less than about 1 wt. % plant lipids.

In specific embodiments, the botanical extract includes less than about 0.5 wt. % plant lipids.

In specific embodiments, the botanical extract includes less than about 5 wt. % plant pigments.

In specific embodiments, the botanical extract includes less than about 1 wt. % plant pigments.

In specific embodiments, the botanical extract includes less than about 0.5 wt. % plant pigments.

In specific embodiments, the botanical extract includes less than about 5 wt. % chlorophylls.

In specific embodiments, the botanical extract includes less than about 1 wt. % chlorophylls.

In specific embodiments, the botanical extract includes less than about 0.5 wt. % chlorophylls.

In specific embodiments, the botanical extract includes at least about 50 wt. %, in the aggregate, of kavalactones, tetrahydrocannabinols (THCs), cannabidiol (CBD), and cannabinoids.

In specific embodiments, the botanical extract includes at least about 70 wt. %, in the aggregate, of kavalactones, tetrahydrocannabinols (THCs), cannabidiol (CBD), and cannabinoids.

In specific embodiments, the botanical extract includes at least about 75 wt. %, in the aggregate, of kavalactones, tetrahydrocannabinols (THCs), cannabidiol (CBD), and cannabinoids.

In specific embodiments, the botanical extract includes at least about 80 wt. %, in the aggregate, of kavalactones, tetrahydrocannabinols (THCs), cannabidiol (CBD), and cannabinoids.

In specific embodiments, the active ingredient is present in at least about 20 wt. %.

In specific embodiments, the active ingredient is present in at least about 25 wt. %.

In specific embodiments, the active ingredient is present in at least about 30 wt. %.

In specific embodiments, the active ingredient is present in at least about 35 wt. %.

In specific embodiments, the active ingredient is present in at least about 40 wt. %.

In specific embodiments, the active ingredient is present in up to about 50 wt. %.

In specific embodiments, the active ingredient is present in up to about 45 wt. %.

In specific embodiments, the active ingredient is present in up to about 40 wt. %.

In specific embodiments, the active ingredient is present in up to about 35 wt. %.

In specific embodiments, the active ingredient is present in about 25-45 wt. %.

In specific embodiments, the active ingredient is present in about 25-40 wt. %.

In specific embodiments, the active ingredient is at least partially encapsulated by the lipid.

In specific embodiments, at least about 10 wt. % of the active ingredient is encapsulated by the lipid.

In specific embodiments, at least about 25 wt. % of the active ingredient is encapsulated by the lipid.

In specific embodiments, at least about 35 wt. % of the active ingredient is encapsulated by the lipid.

In specific embodiments, at least about 50 wt. % of the active ingredient is encapsulated by the lipid.

In specific embodiments, at least about 60 wt. % of the active ingredient is encapsulated by the lipid.

In specific embodiments, at least about 75 wt. % of the active ingredient is encapsulated by the lipid.

In specific embodiments, at least about 85 wt. % of the active ingredient is encapsulated by the lipid.

In specific embodiments, at least about 90 wt. % of the active ingredient is encapsulated by the lipid.

In specific embodiments, at least about 95 wt. % of the active ingredient is encapsulated by the lipid.

In specific embodiments, up to about 99 wt. % of the active ingredient is encapsulated by the lipid.

In specific embodiments, up to about 90 wt. % of the active ingredient is encapsulated by the lipid.

In specific embodiments, up to about 75 wt. % of the active ingredient is encapsulated by the lipid.

In specific embodiments, up to about 50 wt. % of the active ingredient is encapsulated by the lipid.

In specific embodiments, the active ingredient is completely encapsulated by the lipid.

In specific embodiments, the lipid encapsulates the active ingredient by the formation of liposomes and/or micelles.

In specific embodiments, the lipid encapsulates the active ingredient by the formation of liposomes.

In specific embodiments, the lipid encapsulates the active ingredient by the formation of unilamellar liposomes.

In specific embodiments, the lipid encapsulates the active ingredient by the formation of multilamellar liposomes.

In specific embodiments, the lipid encapsulates the active ingredient by the formation of micelles.

In specific embodiments, the film is configured and formulated for the immediate release (IR) of at least one of kavalactones, tetrahydrocannabinols (THCs), cannabidiol (CBD), and cannabinoids.

In specific embodiments, the film is configured and formulated for the sustained release (SR), delayed release (DR), modified release (MR), extended release (XR), or controlled release (CR) of at least one of kavalactones, tetrahydrocannabinols (THCs), cannabidiol (CBD), and cannabinoids.

In specific embodiments, the film is configured and formulated for the sustained release (SR) of at least one of kavalactones, tetrahydrocannabinols (THCs), cannabidiol (CBD), and cannabinoids.

In specific embodiments, the film is configured and formulated for the delayed release (DR) of at least one of kavalactones, tetrahydrocannabinols (THCs), cannabidiol (CBD), and cannabinoids.

In specific embodiments, the film is configured and formulated for the modified release (MR) of at least one of kavalactones, tetrahydrocannabinols (THCs), cannabidiol (CBD), and cannabinoids.

In specific embodiments, the film is configured and formulated for the extended release (XR) of at least one of kavalactones, tetrahydrocannabinols (THCs), cannabidiol (CBD), and cannabinoids.

In specific embodiments, the film is configured and formulated for the controlled release (CR) of at least one of kavalactones, tetrahydrocannabinols (THCs), cannabidiol (CBD), and cannabinoids.

In specific embodiments, the botanical extract includes at least about 50 wt. %, in the aggregate, of kavalactones, tetrahydrocannabinols (THCs), cannabidiol (CBD), and cannabinoids.

In specific embodiments, the botanical extract is enriched with at least one of kavalactones, tetrahydrocannabinols (THCs), cannabidiol (CBD), and cannabinoids.

In specific embodiments, the botanical extract is enriched with tetrahydrocannabinols (THCs).

In specific embodiments, the botanical extract is enriched with cannabidiol (CBD).

In specific embodiments, the botanical extract is enriched with cannabinoids.

In specific embodiments, the thin film is palatable to a human.

In specific embodiments, the external surfaces of the thin film have a smooth texture.

In specific embodiments, the thin film has a high tensile strength.

In specific embodiments, the thin film is pliable.

In specific embodiments, the thin film is non-sticky to touch.

In specific embodiments, the thin film does not readily stick to another thin film.

In specific embodiments, the thin film is relatively soft to touch.

In specific embodiments, the thin film has a chewable configuration.

In specific embodiments, the thin film has a resilient configuration.

In specific embodiments, the thin film has an elastic or malleable configuration.

In specific embodiments, the thin film has a ductile property.

In specific embodiments, the thin film further includes a bitter blocker.

In specific embodiments, the thin film further includes a powder coating present on at least one external surface of the thin film.

In specific embodiments, the thin film further includes a powder coating present on two opposing external surfaces of the thin film.

In specific embodiments, the method of preparing a thin film is carried out in the order indicated.

In specific embodiments, each of the steps of the method of preparing a thin film is carried out in the order indicated.

In specific embodiments, the mixing includes blending.

In specific embodiments, the mixing is carried out at a temperature of about 130-140° F. (54.4-60° C.).

In specific embodiments, the contacting of the active ingredient with the uniform first mixture further includes contacting at least one of a sweetener, flavoring agent, and dye or pigment with the uniform first mixture.

In specific embodiments, the contacting of the binder with the thickened second mixture includes initially contacting a non-sticky binder with the thickened second mixture, and subsequently contacting a sticky binder with the thickened second mixture.

In specific embodiments, the contacting of the binder with the thickened second mixture includes initially contacting microcrystalline cellulose with the thickened second mixture, and subsequently contacting pectin with the thickened second mixture.

In specific embodiments, the condensing includes heating at a temperature of at least about 75° F. (23.9° C.).

In specific embodiments, the condensing includes heating at a temperature of at least about 100° F. (37.8° C.).

In specific embodiments, the condensing includes heating at a temperature of at least about 125° F. (51.7° C.).

In specific embodiments, the condensing includes heating at a temperature of at least about 150° F. (65.6° C.).

In specific embodiments, the condensing includes heating at a temperature of up to about 200° F. (93.4° C.).

In specific embodiments, the condensing includes heating at a temperature of up to about 150° F. (65.6° C.).

In specific embodiments, the condensing includes heating at a temperature of about 75° F. (23.9° C.) to about 200° F. (93.4° C.).

In specific embodiments, the condensing includes heating at a temperature of about 75° F. (23.9° C.) to about 175° F. (79.4° C.).

In specific embodiments, the condensing includes heating at a temperature of about 75° F. (23.9° C.) to about 150° F. (65.6° C.).

In specific embodiments, the condensing is carried out for at least about 10 minutes.

In specific embodiments, the condensing is carried out for at least about 30 minutes.

In specific embodiments, the condensing is carried out for at least about 1 hour.

In specific embodiments, the condensing is carried out for at least about 2 hours.

In specific embodiments, the condensing is carried out for at least about 6 hours.

In specific embodiments, the condensing is carried out for at least about 8 hours.

In specific embodiments, the condensing is carried out for at least about 12 hours.

In specific embodiments, the condensing is carried out for at least about 18 hours.

In specific embodiments, the condensing is carried out for at least about 24 hours.

In specific embodiments, the condensing is carried out for at least about 48 hours.

In specific embodiments, the condensing includes heating with passive convection.

In specific embodiments, the condensing includes heating with active convection.

In specific embodiments, the condensing is carried out in vacuo.

In specific embodiments, the method of preparing a thin film further includes contacting a powder coating with at least one external surface of the thin film.

In specific embodiments, the method of preparing a thin film further includes contacting a powder coating with two opposing external sides of the thin film.

In specific embodiments, the system includes at least about 2 thin films.

In specific embodiments, the system includes at least about 5 thin films.

In specific embodiments, the system includes at least about 10 thin films.

In specific embodiments, the system includes at least about 25 thin films.

In specific embodiments, each of the multiple thin films of the system independently has a dimension of at least 15 mm×25 mm.

In specific embodiments, each of the multiple thin films of the system independently has a dimension of up to 35 mm×50 mm.

In specific embodiments, each of the multiple thin films of the system independently has a dimension of 23 mm×38 mm, ±5 mm.

In specific embodiments, each of the multiple thin films of the system independently has a dimension of 23 mm×38 mm, ±3 mm.

In specific embodiments, each of the multiple thin films of the system independently has a thickness of about 0.01 mm to about 20 mm.

In specific embodiments, each of the multiple thin films of the system independently has a thickness of at least about 0.01 mm.

In specific embodiments, each of the multiple thin films of the system independently has a thickness of up to about 20 mm.

In specific embodiments, each of the multiple thin films of the system independently has a thickness of about 0.03 mm to about 1 mm.

In specific embodiments, each of the multiple thin films of the system independently weighs about 10 mg to about 80 mg.

In specific embodiments, each of the multiple thin films of the system independently weighs at least about 10 mg.

In specific embodiments, each of the multiple thin films of the system independently weighs about up to about 80 mg.

In specific embodiments, each of the multiple thin films of the system independently weighs about 20 mg to about 70 mg.

In specific embodiments, each of the multiple thin films of the system independently weighs at least about 30 mg.

In specific embodiments, each of the multiple thin films of the system independently weighs up to at least about 400 mg.

In specific embodiments, each of the multiple thin films of the system independently weighs about 30 mg to about 400 mg.

In specific embodiments, each of the multiple thin films of the system independently weighs about 60 mg to about 300 mg.

Enumerated Embodiments

Specific enumerated embodiments [1] to [107] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

[1.] An oral dissolvable film that includes:
  (a) solvent,
  (b) binder,
  (c) optionally a lipid,
  (d) emulsifier,
  (e) botanical extract,
  (f) optionally a dough conditioner,
  (g) optionally a flavoring agent,
  (h) optionally a sweetener,
  (i) optionally a dye or pigment,
  (j) a powder coating on at least one external surface, and
  (k) optionally a preservative.

[2.] The oral dissolvable film of claim 1, wherein the botanical extract includes less than about 1 wt. % plant waxes.

[3.] The oral dissolvable film of claim 1, wherein the botanical extract includes less than about 1 wt. % plant lipids.

[4.] The oral dissolvable film of claim 1, wherein the botanical extract includes less than about 1 wt. % plant pigments.

[5.] The oral dissolvable film of claim 1, wherein the botanical extract includes less than about 1 wt. % chlorophylls.

[6.] The oral dissolvable film of claim 1, wherein the botanical extract includes at least about 70 wt. % in the aggregate of kavalactones, tetrahydrocannabinols (THCs), cannabidiol (CBD), and cannabinoids.

[7.] The oral dissolvable film of claim 1, wherein at least about 50 wt. % of the botanical extract is encapsulated by the lipid.

[8.] The oral dissolvable film of claim 1, wherein the botanical extract is present in at least about 20 wt. % of the thin film.

[9.] The oral dissolvable film of claim 1, configured and formulated for the immediate release (IR) of at least one of kavalactones, tetrahydrocannabinols (THCs), cannabidiol (CBD), and cannabinoids.

[10]. The oral dissolvable film of claim 1, configured and formulated for the sustained release (SR), delayed release (DR), modified release (MR), extended release (XR), or controlled release (CR) of at least one of kavalactones, tetrahydrocannabinols (THCs), cannabidiol (CBD), and cannabinoids.

[11]. The oral dissolvable film of claim 1, wherein the dough conditioner includes at least one of glycerin, ethoxylated monoglycerides, and ethoxylated diglycerides.

[12.] The thin film of the above embodiment, wherein the solvent includes at least one of water and ethanol.

[13.] The thin film of any one of the above embodiments, wherein the solvent is present in about 2-24 wt. %.

[14.] The thin film of any one of the above embodiments, wherein the solvent is present in about 4-12 wt. %.

[15.] The thin film of any one of the above embodiments, wherein the solvent is present in about 8 wt. %.

[16.] The thin film of any one of the above embodiments, wherein the binder includes at least one of pectin, microcrystalline cellulose, xanthan gum, locust bean gum, guar gum, gum arabic, gum tragacanth, gum karaya, beta glucan, glucomannan, tapioca starch, carrageenan, xanthan gum, gellan gum, alginic acid or sodium alginate, konjac gum, tara gum, chitosan, agar, maltodextrin, polyvinyl alcohol, pullulan, polycarbophil, povidone, hydroxypropyl methylcellulose, hydroxypropyl cellulose, hydroxypropyl starch, and polyethylene glycol.

[17.] The thin film of any one of the above embodiments, wherein the binder is acidic.

[18.] The thin film of any one of the above embodiments, wherein the binder is present in about 4-50 wt. %.

[19.] The thin film of any one of the above embodiments, wherein the binder is present in about 10-36 wt. %.

[20.] The thin film of any one of the above embodiments, wherein the binder is present in about 25 wt. %.

[21.] The thin film of any one of the above embodiments, wherein the lipid is absent.

[22.] The thin film of any one of the above embodiments, wherein the lipid is present.

[23.] The thin film of any one of the above embodiments, wherein the lipid includes at least one of almond oil, argan oil, avocado oil, canola oil, cashew oil, castor oil, cocoa butter (e.g., deodorized cocoa butter oil), coconut oil, colza oil, corn oil, cottonseed oil, grape seed oil, hazelnut oil, hemp oil, hydroxylated lecithin, lecithin, linseed oil, macadamia oil, mango butter, marula oil, mongongo nut oil, olive oil, palm kernel oil palm oil, peanut oil, pecan oil, perilla oil, pine nut oil, pistachio oil, poppy seed oil, pumpkin seed oil, rice bran oil, safflower oil, sesame oil, Shea butter, soybean oil, sunflower oil, walnut oil, grape seed oil, and watermelon seed oil.

[24.] The thin film of any one of the above embodiments, wherein the lipid is present in about 0-22 wt. %.

[25.] The thin film of any one of the above embodiments, wherein the lipid is present in about 4-22 wt. %.

[26.] The thin film of any one of the above embodiments, wherein the lipid is present in about 10-18 wt. %.

[27.] The thin film of any one of the above embodiments, wherein the lipid is present in about 14.8 wt. %.

[28.] The thin film of any one of the above embodiments, wherein the emulsifier includes at least one of glycerin, propylene glycol, and polyethylene glycol.

[29.] The thin film of any one of the above embodiments, wherein the emulsifier is present in about 3-22 wt. %.

[30.] The thin film of any one of the above embodiments, wherein the emulsifier is present in about 8-18 wt. %.

[31.] The thin film of any one of the above embodiments, wherein the emulsifier is present in about 14 wt. %.

[32.] The thin film of any one of the above embodiments, further including a flavoring agent.

[33.] The thin film of any one of the above embodiments, further including a flavoring agent, including at least one of a liquid flavor extract and a solid flavor extract.

[34.] The thin film of any one of the above embodiments, further including a sweetener.

[35.] The thin film of any one of the above embodiments, further including a sweetener selected from at least one of sucralose, acesulfame potassium, ammonium glycyrrhizinate, naringin dihydrochalcone, neohesperidin dihydrochalcone, neotame, erythritol, xylitol, sucrose, sodium saccharine, stevia, alitame, fructose, and aspartame.

[36.] The thin film of any one of the above embodiments, further including a sweetener, present in about 1-40 wt. %.

[37.] The thin film of any one of the above embodiments, further including a sweetener, present in about 6-14 wt. %.

[38.] The thin film of any one of the above embodiments, further including a sweetener, present in about 10 wt. %.

[39.] The thin film of any one of the above embodiments, further including a dye or pigment.

[40.] The thin film of any one of the above embodiments, further including a dye or pigment selected from at least one of FD&C food colorings and vegetable derived food colorings.

[41.] The thin film of any one of the above embodiments, further including a dye or pigment, present in about 0-0.1 wt. %.

[42.] The thin film of any one of the above embodiments, further including a dye or pigment, present in about 0.01-0.04 wt. %.

[43.] The thin film of any one of the above embodiments, further including a dye or pigment, present in about 0.2 wt. %.

[44.] The thin film of any one of the above embodiments, further including a preservative.

[45.] The thin film of any one of the above embodiments, further including a preservative selected from at least one of benzoate salt (e.g., sodium benzoate), sorbate salt (e.g., sodium sorbate), methyl paraben, propyl paraben, and natamycin.

[46.] The thin film of any one of the above embodiments, further including a preservative, present in about 0-0.1 wt. %.

[47.] The thin film of any one of the above embodiments, further including a preservative, present in about 0-0.02 wt. %.

[48.] The thin film of any one of the above embodiments, further including a dough conditioner.

[49.] The thin film of any one of the above embodiments, further including a dough conditioner that includes at least one of glycerin, ethoxylated monoglycerides, and ethoxylated diglycerides.

[50.] The thin film of any one of the above embodiments, further including a dough conditioner that includes glycerin.

[51.] The thin film of any one of the above embodiments, further including a dough conditioner that includes ethoxylated monoglycerides.

[52.] The thin film of any one of the above embodiments, further including a dough conditioner that includes ethoxylated diglycerides.

[53.] The thin film of any one of the above embodiments, further including a dough conditioner present in about 0-25 wt. %.

[54.] The thin film of any one of the above embodiments, further including a dough conditioner present in about 1-25 wt. %.

[55.] The thin film of any one of the above embodiments, further including a dough conditioner present in about 1-15 wt. %.

[56.] The thin film of any one of the above embodiments, further including a powder coating.

[57.] The thin film of any one of the above embodiments, further including a powder coating selected from at least one of talc, microcrystalline cellulose, flavoring agent (e.g., mint flavoring), sweetener (e.g., sucralose and/or acesulfame potassium), and tapioca starch.

[58.] The thin film of any one of the above embodiments, further including a powder coating, present in about 0-20 wt. %.

[59.] The thin film of any one of the above embodiments, further including a powder coating, present in about 5-15 wt. %.

[60.] The thin film of any one of the above embodiments, further including a powder coating, present in about 10 wt. %.
[61.] The thin film of any one of the above embodiments, wherein the active ingredient is present in at least about 25 wt. %.
[62.] The thin film of any one of the above embodiments, wherein the active ingredient is present in at least about 30 wt. %.
[63.] The thin film of any one of the above embodiments, wherein the active ingredient is present in at least about 35 wt. %.
[64.] The thin film of any one of the above embodiments, wherein the active ingredient is present in at least about 40 wt. %.
[65.] The thin film of any one of the above embodiments, wherein the active ingredient is present in about 25-40 wt. %.
[66.] The thin film of any one of the above embodiments, wherein the active ingredient is at least partially encapsulated by the lipid.
[67.] The thin film of any one of the above embodiments, wherein at least about 25 wt. % of the active ingredient is encapsulated by the lipid.
[68.] The thin film of any one of the above embodiments, wherein at least about 50 wt. % of the active ingredient is encapsulated by the lipid.
[69.] The thin film of any one of the above embodiments, wherein at least about 75 wt. % of the active ingredient is encapsulated by the lipid.
[70.] The thin film of any one of the above embodiments, the active ingredient is completely encapsulated by the lipid.
[71.] The thin film of any one of the above embodiments, which is palatable to a human.
[72.] The thin film of any one of the above embodiments, wherein the external surfaces have a smooth texture.
[73.] The thin film of any one of the above embodiments, which has a high tensile strength.
[74.] The thin film of any one of the above embodiments, which is pliable.
[75.] The thin film of any one of the above embodiments, which is non-sticky to touch.
[76.] The thin film of any one of the above embodiments, which does not readily stick to another thin film.
[77.] The thin film of any one of the above embodiments, which is relatively soft to touch.
[78.] The thin film of any one of the above embodiments, having a chewable configuration.
[79.] The thin film of any one of the above embodiments, having a resilient configuration.
[80.] The thin film of any one of the above embodiments, having an elastic or malleable configuration.
[81.] The thin film of any one of the above embodiments, including a ductile property.
[82.] The thin film of any one of the above embodiments, further including a bitter blocker.
[83.] The thin film of any one of the above embodiments, further including a powder coating present on at least one external surface of the thin film.
[84.] The thin film of any one of the above embodiments, further including a powder coating present on two opposing external surfaces of the thin film.
[85.] The thin film of any one of embodiments [83]-[84], wherein the powder coating includes at least one of talc and microcrystalline cellulose.
[86.] A thin film that includes:
    (a) about 2-24 wt. % solvent,
    (b) about 4-50 wt. % binder,
    (c) about 0-10 wt. % flavoring agent,
    (d) about 1-40 wt. % sweetener,
    (e) about 4-22 wt. % lipid,
    (f) about 3-22 wt. % emulsifier,
    (g) about 0-1.0 wt. % dye or pigment,
    (h) about 0-0.1 wt. % preservative,
    (i) up to about 65 wt. % active ingredient, and
    (j) about 0-20 wt. % powder coating.
[87.] A thin film that includes:
    (a) solvent including water,
    (b) binder including pectin,
    (c) optionally a lipid including at least one of deodorized cocoa butter oil, fruit seed oil, and vegetable based oil,
    (d) emulsifier including at least one of glycerin, ethoxylated monoglycerides, and ethoxylated diglycerides,
    (e) botanical extract,
    (f) flavoring agent including mint flavoring
    (g) sweetener including at least one of sucralose and acesulfame potassium,
    (h) dye or pigment including at least one of FD&C red, FD&C blue, and FD&C yellow,
    (i) a powder coating on at least one external surface, including at least one of talc, microcrystalline cellulose, mint flavoring, sucralose, acesulfame potassium, and tapioca starch, and
    (j) optionally a preservative including at least one of sodium benzoate, methyl paraben, propyl paraben, and sodium sorbate.
[88.] A method of preparing a thin film, the method includes:
    (a) mixing a lipid (optional), emulsifier, and solvent to provide a uniform first mixture;
    (b) contacting an active ingredient with the uniform first mixture to provide a thickened second mixture;
    (c) contacting a binder with the thickened second mixture to provide a slurry; and
    (d) hot extruding, casting, and condensing the slurry to provide the thin film; or cooling, shearing, mixing, casting, and condensing the slurry to provide the thin film.
[89.] The method of the above embodiment, wherein the thin film obtained is a thin film as described in any one of the above embodiments (e.g., any one of embodiments [1]-[87]).
[90.] The method of any one of the above embodiments, wherein the mixing includes blending.
[91.] The method of any one of the above embodiments, wherein the mixing is carried out at a temperature of about 130-140° F. (54.4-60° C.).
[92.] The method of any one of the above embodiments, wherein the contacting of the active ingredient with the uniform first mixture further includes contacting at least one of a sweetener, flavoring agent, and dye or pigment with the uniform first mixture.
[93.] The method of any one of the above embodiments, wherein the contacting of the binder with the thickened second mixture includes initially contacting a non-sticky binder with the thickened second mixture, and subsequently contacting a sticky binder with the thickened second mixture.
[94.] The method of any one of the above embodiments, wherein the contacting of the binder with the thickened second mixture includes initially contacting microcrystalline cellulose with the thickened second mixture, and subsequently contacting pectin with the thickened second mixture.

[95.] The method of any one of the above embodiments, wherein the condensing includes heating at a temperature of at least about 50° F. (10° C.).
[96.] The method of any one of the above embodiments, wherein the condensing is carried out for at least about 10 minutes.
[97.] The method of any one of the above embodiments, wherein the condensing includes heating with passive convection.
[98.] The method of any one of the above embodiments, wherein the condensing includes heating with active convection.
[99.] The method of any one of the above embodiments, wherein the condensing is carried out in vacuo.
[100.] The method of any one of the above embodiments, further including contacting a powder coating with at least one external surface of the thin film.
[101.] The method of any one of the above embodiments, further including contacting a powder coating with two opposing external sides of the thin film.
[102.] The method of any one of embodiments [88]-[101], wherein the powder coating includes at least one of talc and microcrystalline cellulose.
[103.] A system that includes:
(a) multiple thin films, each in direct contact with at least one other thin film, and each independently described in any one of the above embodiments (e.g., any one of embodiments [1]-[87]);
(b) packaging material enclosing the multiple thin films; and
(c) printed indicia located on the packaging material;
wherein the multiple thin films do not readily stick to another.
[104.] The system of the above embodiment, including at least about 5 thin films.
[105.] The system of any one of the above embodiments, including up to about 25 thin films.
[106.] The system of any one of the above embodiments, wherein each of the multiple thin films independently has a dimension of 23 mm×38 mm, ±3 mm.
[107.] The system of any one of the above embodiments, wherein each of the multiple thin films is independently prepared as described in any one of the above embodiments (e.g., any one of embodiments [88]-[102]).

The invention will now be described by the following non-limiting examples.

EXAMPLES

Example 1

Preparation of Thin Film with an Encapsulated Active Ingredient

Liposomes can be prepared by using a phospholipid like hydroxylated lecithin, an oil such as deodorized cocoa butter, water, and glycerin. These substances are mixed (warm), so the cocoa butter is melted, using a high shear blender or a hand-held mixer. To this is added the active ingredient, whether they are water-soluble or fat-soluble. A high shear blender can be employed. The active ingredient can be incorporated into the layers of the forming liposomes. After the formation of the active impregnated liposomes, the following substances can be added: flavorings, sweeteners, colors, non-sticky binders (e.g., microcrystalline cellulose), and finally a sticky binder (e.g., pectin). This slurry is now a colloid consisting of liposomes dispersed in an aqueous hydrogel.

The slurries are typically 60-80% water. They can be spread onto glass in the laboratory or onto PET (polyethylene terephthalate) film in the factory and cooked at 60-105° C. both in laboratory and factory settings. The slurries can be hardened into flexible films that are 4-22% water when cooking is complete. Further cooking leads to brittle and eventually charred products. Laboratory films are typically cut and packaged as soon as they are out of the oven. The hardened films from the factory are cured for 1-4 days then slit, cut, and packaged. The films cannot be over-cured, so sometimes longer cure times happen due to time and availability of working staff. Driving off of water from a warm and pliable slurry is believed to yield metamorphosed liposomal structures now suspended in close proximity in a solid wafer film. Curing completes the metamorphosis. Without being bound to any particular theory, there is believed to be a plurality of liposomal structures, and even multilayer lipid bilayer sheets in the final products.

Example 2

Exemplary Formulations, Oral Thin Film

| Ingredient | Amount present | Amount present | Amount present |
|---|---|---|---|
| solvent | 2-24 wt. % | 4-12 wt. % | 8 wt. % |
| binder | 4-50 wt. % | 10-36 wt. % | 25 wt. % |
| flavoring agent | 0-10 wt. % | 2-4 wt. % | 4 wt. % |
| sweetener | 0-40 wt. % | 6-14 wt. % | 9.5 wt. % |
| lipid | 0-22 wt. % | 10-18 wt. % | 14.8 wt. % |
| emulsifier | 3-22 wt. % | 8-18 wt. % | 14 wt. % |
| dye or pigment | 0-1.0 wt. % | 0.01-0.04 wt. % | 0.02 wt. % |
| preservative | 0-0.1 wt. % | 0-0.02 wt. % | 0 wt. % |
| active ingredient: botanical extract | up to about 65 wt. % | up to about 40 wt. % | about 33 wt. % |
| powder coating | 0-20 wt. % | 5-15 wt. % | 10 wt. % |

Note:
In the above formulations, the finished product may include about 8-10 wt. % moisture.

Example 3

Exemplary Formulations, Oral Thin Film

| Ingredient | Amount present | Amount present | Amount present |
|---|---|---|---|
| water | 2-24 wt. % | 4-12 wt. % | 8 wt. % |
| pectin and microcrystalline cellulose | 4-50 wt. % | 10-36 wt. % | 25 wt. % |
| mint flavoring | 0-10 wt. % | 2-4 wt. % | 4 wt. % |
| sucralose, acesulfame potassium, and/or ammonium glycyrrhizinate | 0-40 wt. % | 6-14 wt. % | 9.5 wt. % |
| hydroxylated lecithin, deodorized cocoa butter, fruit seed oil, and/or vegetable based oil | 0-22 wt. % | 10-18 wt. % | 14.8 wt. % |
| glycerin, ethoxylated | 3-22 wt. % | 8-18 wt. % | 14 wt. % |

-continued

| Ingredient | Amount present | Amount present | Amount present |
|---|---|---|---|
| monoglycerides, and/or ethoxylated diglycerides | | | |
| FD&C food colorings | 0-1.0 wt. % | 0.01-0.04 wt. % | 0.02 wt. % |
| sodium benzoate | 0-0.1 wt. % | 0-0.02 wt. % | 0 wt. % |
| active ingredient: botanical extract | up to about 65 wt. % | up to about 40 wt. % | about 33 wt. % |
| powder coating of talc, microcrystalline cellulose, powdered flavoring, and/or sweetener | 0-20 wt. % | 5-15 wt. % | 10 wt. % |

Note:
In the above formulations, the finished product may include about 8-10 wt. % moisture.

Example 4

Oral Dissolvable Film Containing Kavalactones

The goal of this procedure is to produce a 38 mm×23 mm, 120 mg total weight film, containing 18 mg of kavalactones botanical extract.

This mixture used a total of 356 mL water. The water was heated in a 400 mL polypropylene beaker in a microwave oven to about 60° C.

To a mass of 18.5 g of glycerin, 5.08 g of hydroxylated soy lecithin, and 5.64 g of deodorized cocoa butter in a 100 mL glass beaker was added 40 mL of 60° C. water. The mixture was stirred with a metal spatula until the cocoa butter was fully melted and the contents are uniformly mixed (about 1-2 minutes). This mixture was poured into a blender. The beaker was rinsed with 80 mL, 60° C. water. This rinse water was poured into the mixture in the blender. The remainder of the hot water was added to the blender.

With stirring on low, 18.5 g of 75% kavalactones (previously extracted from kava roots using supercritical carbon dioxide) was added. After stirring on a low setting, about 1 minute, the ingredients were thoroughly mixed and distributed. With mixing, the following ingredients were added in order: 3.70 g A.M. Todd's Crystal White®, 5.54 g sucralose, 2.77 g acesulfame potassium, 3.70 g 50 µm microcrystalline cellulose, and 12 mg FD&C blue #1. In a rapid fashion, over about 5-10 seconds, is added 29.0 g C.P. Kelco's Slow Set Genu® Pectin. The mixture was stirred from low to high speeds until smooth, or for about 3 minutes.

The slurry from above was spread onto 12 inch×16 inch tempered glass plates using a ⅝ inch diameter glass rod with 17 gauge Nichrome wire depth gauges. The plates were cooked in a 70° C. convection oven for about 20 minutes. Upon removal, the plates were cooled and the film was cut using a razorblade and stainless steel cutting templates to yield 38 mm×23 mm strips that weigh about 120 mg each.

Example 5

Oral Dissolvable Film Containing Kavalactones, CBD, and THC

The goal of this pro-cedure was to produce a 38 mm×23 mm, 120 mg total weight film, containing 18 mg of kavalactones, 5 mg industrial hemp-derived cannabidiol (CBD), and 1.7 mg industrial hemp-derived tetrahydrocannabinol (THC) botanical extracts.

This mixture will used a total of 230 mL water. The water was heated in a 400 mL poly-propylene beaker in a microwave oven to about 60° C.

To a mass of 18.0 g glycerin, 5.50 g hydroxylated lecithin, and 6.10 g Captex® 355 (medium chain fractionated coconut oil) in a 100 mL glass beaker was added 40 mL of 60° C. water. The mixture was stirred with a metal spatula until the materials are evenly disbursed (30-60 seconds). The mixture was poured into a 1 L stainless steel solid flatware cylinder. The beaker was rinsed with 80 mL, 60° C. water. This rinse water was poured into the mixture in the stainless steel solid flatware cylinder. The remainder of the hot water was added to the stainless steel solid flatware cylinder.

To the mixture was added 20.0 g of 75% kavalactones (previously extracted from kava roots using supercritical carbon dioxide). The mixture was stirred with a with a handheld, high-shear mixer until the mixture was homogenous. To the mixture was added 7.38 g of industrial hemp botanical extract that is 56.44% CBD, 19.65% THC. The mixture was further stirred with a with a handheld, high-shear mixer for about 1 minute until the ingredients were thoroughly mixed and distributed. With mixing, the following ingredients were added in order: 4.00 g A.M. Todd's Crystal White®, 6.00 g sucralose, 3.00 g acesulfame potassium (ACE-K), and 4.00 g 50 µm microcrystalline cellulose. In a rapid fashion, over about 5-10 seconds, was added 26.0 g C.P. Kelco's Slow Set Genu® Pectin. The mixture was stirred with a with a handheld, high-shear mixer until smooth, or for about 3 minutes.

The slurry was then spread onto glass plates using a 12×16 inch tempered glass sheet and a glass rod fitted with 18 gauge Nichrome wire depth gauges. The plates were cooked in a convection oven for about 15 minutes at 70° C. The film was cut using templates and razor blade. The individual film doses were separated from the glass plates with a razor blade.

Example 6

Oral Dissolvable Film, Lipid Free, Containing Kavalactones, CBD, and THC

The goal of this procedure was to produce a 38 mm×23 mm, 140 mg total weight film, containing 18 mg of kavalactones, 5.0 mg industrial hemp-derived cannabidiol (CBD), and 1.7 mg industrial hemp-derived tetrahydrocannabinol (THC) botanical extracts.

This mixture used a total of 220 mL water. The water was heated in a 400 mL poly-propylene beaker in a microwave oven to about 60° C.

To a mass of 17.0 g glycerin and 19.0 g PEG-1000 in a 100 mL glass beaker was added 40 mL of 60° C. water. The mixture was stirred with a metal spatula until the materials were evenly disbursed (30-60 seconds). The mixture was poured into a 1 L stainless steel solid flatware cylinder. The beaker was rinsed with 80 mL, 60° C. water. This rinse water was poured into the mixture in the stainless steel solid flatware cylinder. The remainder of the hot water was added to the stainless steel solid flatware cylinder.

To the mixture was added 17.1 g of 75% kavalactones (previously extracted from kava roots using supercritical carbon dioxide). The mixture was stirred with a with a handheld, high-shear mixer until the mixture was homogenous. To the mixture was added 6.33 g of industrial hemp botanical extract that was 56.44% CBD, 19.65% THC. The mixture was further stirred with a with a handheld, high-shear mixer for about 1 minute until the ingredients were thoroughly mixed and distributed. With mixing, the following ingredients were added in order: 4.00 g A.M. Todd's Crystal White®, 6.00 g sucralose, 3.00 g acesulfame potassium (ACE-K), and 3.00 g 50 µm microcrystalline cellulose (FMC's Endurance®). In a rapid fashion, over about 5-10 seconds, was added 24.6 g C.P. Kelco's Slow Set Genu® Pectin. The mixture was stirred with a with a handheld, high-shear mixer until smooth, or for about 3 minutes.

The slurry was then spread onto glass plates using a 12×16 inch tempered glass sheet and a glass rod fitted with 18 gauge Nichrome wire depth gauges. The plates were cooked in a convection oven for about 15 minutes at 70° C. The film was cut using templates and razor blade. The individual film doses were separated from the glass plates with a razor blade.

What is claimed is:

1. An oral dissolvable thin film comprising effective amounts of:
   (a) water;
   (b) a binder selected from the group consisting of pectin, microcrystalline cellulose, and combinations thereof;
   (c) a lipid, wherein the lipid comprises cocoa butter and lecithin;
   (d) an emulsifier, wherein the emulsifier comprises glycerin;
   (e) at least one cannabinoid, present in an amount of at least about 30 wt. % of the oral dissolvable thin film;
   (f) a flavoring agent selected from the group consisting of mint flavoring, spearmint flavoring, peppermint flavoring, and combinations thereof;
   (g) a sweetener selected from the group consisting of sucralose, acesulfame potassium, and combinations thereof; and
   (h) a powder coating on at least one external surface of the oral dissolvable thin film wherein:
      at least about 10 wt. % of the at least one cannabinoid is encapsulated by the lipid,
      the oral dissolvable thin film has a thickness of about 0.01 mm to about 20 mm, and
      the oral dissolvable thin film has a rapid dissolution of about 30-300.

2. The oral dissolvable film of claim 1, wherein the at least one cannabinoid comprises less than about 1 wt. % plant waxes.

3. The oral dissolvable film of claim 1, wherein the at least one cannabinoid comprises less than about 1 wt. % plant lipids.

4. The oral dissolvable film of claim 1, wherein the at least one cannabinoid comprises less than about 1 wt. % plant pigments.

5. The oral dissolvable film of claim 1, wherein the at least one cannabinoid comprises less than about 1 wt. % chlorophylls.

6. The oral dissolvable film of claim 1, wherein at least about 50 wt. % of the at least one cannabinoid is encapsulated by the lipid.

7. The oral dissolvable film of claim 1, wherein the at least one cannabinoid is present in an amount of at least about 35 wt. % of the thin film.

8. The oral dissolvable film of claim 1, configured and formulated for the immediate release (IR) of the at least one cannabinoid.

9. The oral dissolvable film of claim 1, configured and formulated for the sustained release (SR), delayed release (DR), modified release (MR), extended release (XR), or controlled release (CR) of the at least one cannabinoid.

10. The oral dissolvable film of claim 1, further comprising a dough conditioner selected from the group consisting of glycerin, ethoxylated monoglycerides, ethoxylated diglycerides, and combinations thereof.

11. The oral dissolvable film of claim 1 wherein the pectin is genu pectin.

12. The oral dissolvable film of claim 1 wherein the at least one cannabinoid is selected from the group consisting of tetrahydrocannabinol (THC), cannabidiol (CBD), and combinations thereof.

13. An oral dissolvable thin film comprising effective amounts of:
   (a) about 2 wt. % to 24 wt. % of water;
   (b) about 40 wt. % to 50 wt. % of a binder selected from the group consisting of pectin, microcrystalline cellulose, and combinations thereof;
   (c) about 0.1 wt. % to 22 wt. % of a lipid, wherein the lipid comprises cocoa butter and lecithin;
   (d) about 3 wt. % to 22 wt. % of an emulsifier, wherein the emulsifier comprises glycerin;
   (e) at least about 30 wt. % of at least one cannabinoid;
   (f) greater than 0 wt. % to about 10 wt. % of a flavoring agent selected from the group consisting of mint flavoring, spearmint flavoring, peppermint flavoring, and combinations thereof;
   (g) greater than 0 wt. % to about 40 wt. % of a sweetener selected from the group consisting of sucralose, acesulfame potassium, and combinations thereof;
   (h) greater than 0 wt. % to about 20 wt. % of a powder coating, wherein powder coating is present on at least one external surface of the oral dissolvable thin film; and
   (i) a preservative; wherein:
      at least about 10 wt. % of the at least one cannabinoid is encapsulated by the lipid,
      the oral dissolvable thin film has a thickness of about 0.01 mm to about 20 mm, the oral dissolvable thin film has a rapid dissolution of about 30-300, and the at least one cannabinoid comprises less than about 1 wt. % plant waxes, less than about 1 wt. % plant lipids, less than about 1 wt. % plant pigments, less than about 1 wt. % chlorophylls.

14. The oral dissolvable thin film of claim 1 or 13, further comprising an absorption enhancer.

15. The oral dissolvable thin film of claim 1, further comprising a preservative.

* * * * *